(12) United States Patent
Case et al.

(10) Patent No.: US 7,974,379 B1
(45) Date of Patent: Jul. 5, 2011

(54) METROLOGY AND REGISTRATION SYSTEM AND METHOD FOR LAMINOGRAPHY AND TOMOGRAPHY

(75) Inventors: Thomas A. Case, Walnut Creek, CA (US); Wenbing Yun, Walnut Creek, CA (US); Alan Francis Lyon, Berkeley, CA (US)

(73) Assignee: Xradia, Inc., Concord, CA (US)

(\*) Notice: Subject to any disclaimer, the term of this patent is extended or adjusted under 35 U.S.C. 154(b) by 162 days.

(21) Appl. No.: 12/556,341

(22) Filed: Sep. 9, 2009

Related U.S. Application Data

(60) Provisional application No. 61/095,330, filed on Sep. 9, 2008.

(51) Int. Cl.
*G01N 23/04* (2006.01)

(52) U.S. Cl. .......................................... 378/63; 378/206

(58) Field of Classification Search .................... 378/62, 378/63, 205, 206
See application file for complete search history.

(56) References Cited

U.S. PATENT DOCUMENTS

2005/0069090 A1\* 3/2005 Rafaeli et al. ................. 378/205
\* cited by examiner

*Primary Examiner* — Courtney Thomas
(74) *Attorney, Agent, or Firm* — Houston Eliseeva, LLP

(57) ABSTRACT

A metrology system that uses an imaging system to monitor alignment features on the sample or sample holder of an X-ray laminography or tomography system. the metrology system has the capability to provide both sample shift and sample rotation movement data to a data acquisition system. These shift and rotation data can be used in alignment routines to produce 3D reconstructions from the X-ray images/projections. The metrology system is based on an imaging and focusing measurement of intrinsic feature of the sample or artificial features fabricated on the sample or sample holder.

24 Claims, 3 Drawing Sheets

METROLOGY AND REGISTRATION SYSTEM AND METHOD FOR LAMINOGRAPHY AND TOMOGRAPHY

RELATED APPLICATIONS

This application claims the benefit under 35 USC 119(e) of U.S. Provisional Application No. 61/095,330, filed on Sep. 9, 2008, which is incorporated herein by reference in its entirety.

BACKGROUND OF THE INVENTION

Computed tomography (CT) and laminography systems are able to image three dimensional (3D) structures of samples, particularly their embedded structures and often without any destructive or invasive process. These techniques have found a wide range of applications from non-destructive integrated circuit testing to medical/biological imaging. In these systems, a series of projection images are acquired at different view angles to gain different perspectives of the specimen. These projections are then mathematically assembled to reconstruct a 3D image that represents the 3D structure of the specimen. X-ray radiation is typically used in these applications as it provides a good combination of high penetration, low scattering, and relatively simple absorption characteristics.

A key requirement in producing the 3D images in both CT and laminography systems is that all projections must be aligned so that the sample appears to rotate through a common rotation axis. In most systems with imaging resolutions coarser than tens of micrometers, the mechanical rotation stage accuracy is sufficient to maintain apparent rotation axis in projection images without any additional data processing. In these cases, a simple pre-calibration is need to determine the systematic shift error at each view angle and true rotation center using a well-known test sample. However, with higher resolution imaging systems such as micro-CT or nano-CT systems, the asynchronous error of most mechanical stages will exceed the resolution, and a simple calibration will not be sufficient to maintain the alignment accuracy. In these cases, an additional alignment step is typically needed to remove the shift errors.

Several approaches have been used to mitigate mechanical stage alignment errors. Two commonly used techniques are:

(1) Using intrinsic features in the sample or introducing artificial alignment targets into the sample and align each projection to this target. This approach generally requires some distinct sharp/high-resolution features inside the sample that can be imaged at high-resolution at all view angles. Otherwise, some modification will be required to introduce artificial features into the sample. The later approach is often used in CT with transmission electron microscopes (TEM) when colloidal gold particles are introduced into samples as alignment targets.

(2) Fabricating alignment target on the sample holder and use an integrated metrology system to monitor the position of the sample holder. The monitoring system will produce shift data for each view angle that will be used in the alignment routine. Typical monitoring systems can be based on various technologies such as mechanical micrometers, capacitance sensors, encoders, and laser interferometers, for example.

SUMMARY OF THE INVENTION

The invention concerns a metrology system that uses an imaging system to monitor alignment features on the sample or sample holder and has the capability to provide both sample shift and sample rotation movement data to a data acquisition system. These shift and rotation data can be immediately used in alignment routines to produce 3D reconstructions.

The metrology system is based on an imaging and focusing measurement of intrinsic feature of the sample or artificial features fabricated on the sample or sample holder.

In general, according to one aspect, the invention features, a metrology system integrated into an X-ray laminography or tomography system. The system comprises an illumination source for illuminating an alignment target, an objective lens, a spatially resolved detector for detecting an image of the alignment target formed by the objective lens, and a stage system that rotates a sample of the laminography or tomography system and the alignment target.

In embodiments, the illumination source produces infrared light, visible light, or ultra-violet light. The objective lens has a numerical aperture of 0.1 to 0.9 or is an immersion lens with a numerical aperture of 0.5 to 1.4. 8. A controller shifting images from the laminography or tomography system in response to the images of the alignment target to compensate for errors in the stage system.

In general, according to another aspect, the invention features, metrology method for a an X-ray laminography or tomography system. The method comprises capturing X-ray images of a sample and rotating the sample between images, detecting optical images of the sample or a sample mounting system for each of the X-ray images, determining shifts in the sample between the X-ray images with reference to the optical images, shifting the X-ray images with respect to each other in response to the determined shifts in the optical images, and performing a reconstruction process on the shifted X-ray images to produce a three dimensional image of the sample.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
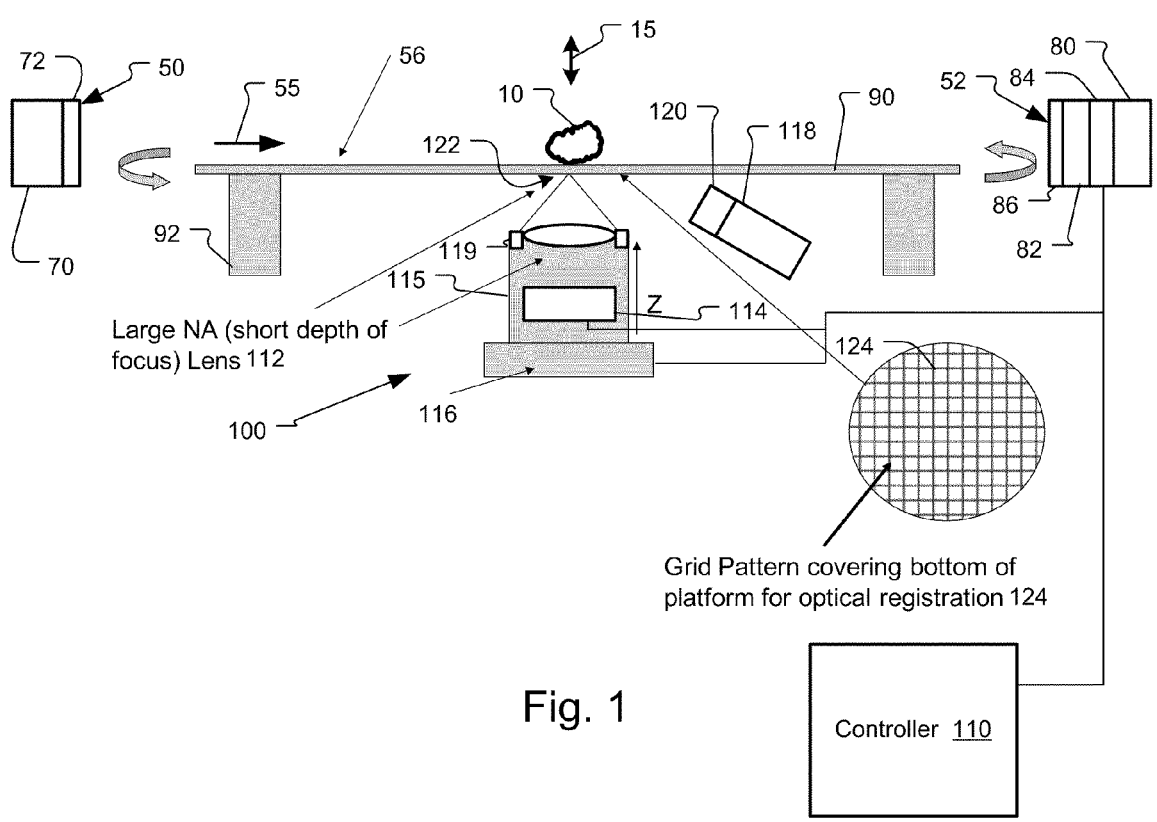
FIG. 1 is a schematic drawing of an exemplary metrology system integrated in a laminography system, the metrology system comprises a sample stage, grid pattern fabricated at the bottom of the sample holder, visible light objective lens, and vertical stage to move the objective lens along the z-axis, and a controller/computer analysis station with center finding analysis algorithm(s) to locate center of features with a resolution better than the intrinsic optical resolution of the imaging system.

FIG. 1 shows an optical metrology system 100 integrated into a 3D imaging system 50, 52, 56 such as CT or laminography system that has been constructed according to the principles of the present invention.

In more detail, 3D imaging system comprises an X-ray source 50 and an X-ray detector 52 that acquire images laterally through the sample 10, at oblique angles through the sample 10 or vertically through the sample 10 depending on the configuration or application. The images detected by the detector 52 are provided to controller 110.

In one example, the X-ray source 50 a synchrotron beam line. In other examples, the source is a laboratory source 70 such as a microfocus source or rotating anode source. In implementations, the X-ray source 50 also includes a condenser 72 for concentrating the X-ray beam 55 on the sample 10.

The X-ray detector 52 in one implementation comprises a charge-coupled device (CCD) or CMOS chip 80 having a two dimensional array of pixels, of at least 1,024×1,024, in a direct detection mode. In other implementations, a scintillator 82 is used to convert the X-ray beam 55 from the sample 10 into optical frequencies, which are then detected by the detector chip 80. Optical imaging lenses 84 are used between the scintillator 82 and detector chip 80 for further magnification in some implementations. In still other examples, an X-ray objective 86 is used between the sample 10 and the chip/scintillator to image and magnify the X-ray image on the chip/scintillator.

The sample 10 is held on a sample mounting plate 90 of a rotary platform and sample stage 56 that rotates the sample 10 in the X-ray beam 55 between the X-ray source 50 and the detector 50 around a rotation axis 15 under control of controller 110.

The metrology system 100, in one example, is based on a visible light imaging system. The metrology system includes visible light illumination source 118 and condenser lens system 120 to project the visible light onto a region of interest (ROI) 122. In the illustrated embodiment, the ROI 122 is on the backside of the sample mounting plate 90 of the rotary platform 56 and opposite the sample 10. The ROI 122 is typically located on the axis of rotation 15 of the rotary platform and sample stage 56. In one implementation, illumination source 118 and condenser lens system 120 are integrated into the objective lens in an in-line epi-illumination design.

A large numerical aperture (NA) objective lens 112 images the ROI 122 onto an optical image detector 114. A grid pattern 124 is fabricated in the ROI 122 on to the sample mounting plate 90 of the rotary platform 56, which holds the sample 10 during the imaging process performed by the X-ray source 50 and detector 52.

Figure 2:
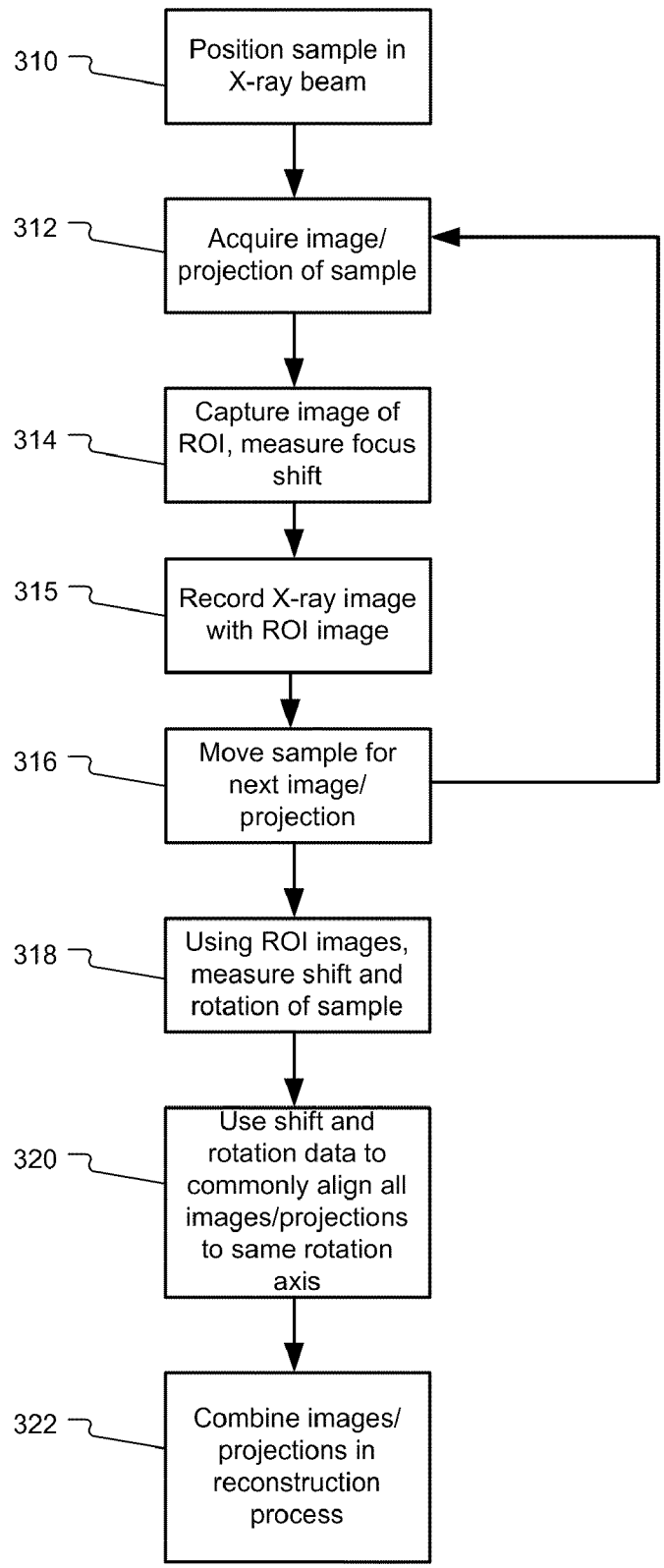
FIG. 2 is a flow diagram illustrating a compensation method for image registration and 3D image reconstruction.

FIG. 2 is flow diagram illustrating the operation of the optical metrology system 100 according to the principles of the present invention.

The metrology system 100 provides measurements of the shifts in the two dimensions defined by the plane of the sample mounting plate 90 and rotation of a sample 10 around axis 15, which extends orthogonal to the mounting plate plane.

In particular, the sample 10 is first aligned in the X-ray beam 55 in step 310. Then, the first X-ray image is acquired by detecting the X-rays from source 50 with detector 52. Contemporaneously, the optical detector 114 captures an image of the ROI 122. The X-ray image is recorded with the image of the ROI 122 in step 315 by the controller 110. The rotary platform 56 is then advanced in step 316 and the next image acquired 312. This process is repeated. For each X-ray image at each angle, an image of the ROI 122 is captured and saved with the corresponding X-ray image by the controller 110.

In step 318, the ROI images are compared to determine sample shift in the two dimensions of the mounting plate 90 and changes in the rotation axis 15 between X-ray images and also the angle of rotation between X-ray images. In one example, the controller 110 executes a center finding algorithm on each ROI image to determine shifts between X-ray images. These position shift and rotation data are then used by a controller/image processor 110 to align the X-ray image projection data, provided by X-ray detector 52, to each other in step 320. The controller 110 aligns the images so that they all appear to rotate around a common rotation axis. The images are individually shifted to be centered on a common nominal axis and the shifted images are used in the reconstruction process performed by the controller 110, in step 322 to produce a 3D image of the sample 10.

The metrology system 100 is based on an imaging system that uses the objective lens 112 to image either an intrinsic feature of the sample 10 or artificial features fabricated on the sample 10 or sample mounting plate 90 to a spatially resolved detector 114. When a lateral sample movement occurs, it is directly recorded by shifts in the image, such as grid pattern 124, recorded by the image detector 114. In the preferred embodiment, the resolution of the shifts is better than 100 nanometers.

In the preferred embodiment, the metrology system 100 also measures vertical sample movements due to errors in the rotary platform 56. The large NA lens 112 yields image defocus when the sample mounting plate 90/sample 10 move vertically. This is measured by making focusing adjustments of the lens 112, specifically the distance between the lens 112 and the detector 114 in one implementation is controlled by an objective lens stage 119. Here, different embodiments are possible. In examples, the lens stage 119 is a mechanical ball-bearing stage, a mechanical roller-bearing stage, or a flexure stage. Drive to the stage 119 is provided by a DC motor, stepper motor, or a piezo-electric motor.

In other examples, the camera assembly 115, including the lens 112 and detector 114 is moved to detect focus shifts. In one example, the camera assembly 115 is supported on a Z-axis actuator 116 that moves the camera assembly 115 toward and away from the backside of sample mounting plate 90 of the rotary platform 56 to maintain focus. Thus shift in the position of the sample holder 56, and thus sample 10, are measured in real time during sample rotation and stored with the associated X-ray image and ROI image in the controller 110.

These vertical shift data are then used by the controller 110 to further align the X-ray images at the different angles relative to each other or adjust the height of the plate 90 between X-ray images to maintain a constant height for vertical sample position.

This metrology system 100 operates with electromagnetic radiation. Various wavelength including infra-red (IR), visible light, and ultraviolet radiation are various alternatives. Selection among the different characteristics of each wavelength is made to optimize the metrology system's capability and performance. For example, visible light offers a wide range of illuminator, lens, and detector options while IR light offers different penetration characteristics in different materials that may be suitable for certain types of samples.

Figures 3A, 3B:
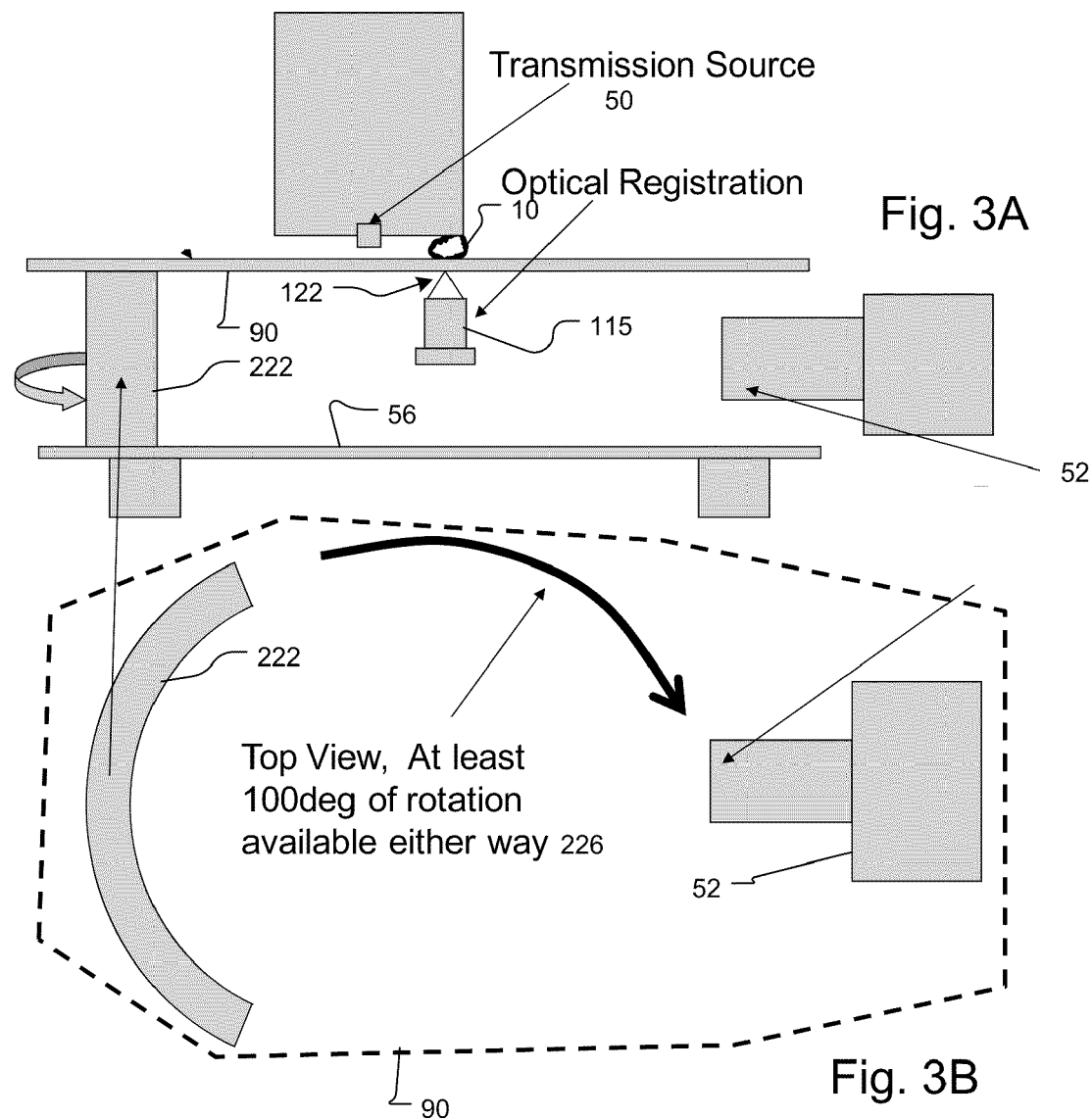
FIGS. 3A and 3B is a schematic side plan and top plan drawings showing the metrology system used in a laminography system.

FIGS. 3A and 3B illustrate an embodiment of the metrology system 100 that is integrated into a low angle laminography system. The sample 10 is carried on a sample mounting plate 90 that is raised above a rotation and translation stage 56 on a beam 222. An x-ray source 50 and spatially resolved x-ray detector 52 are placed on opposite sides of the sample 10. Their motion is typically constrained to be in diametrically opposite direction of the ROI 122 in order to maintain the ROI 122 in the field of view (FOV) of camera assembly 115 and its optical detector. In this configuration, the sample stage 56 provides both lateral translation and rotation motion around the vertical axis under control of a controller. A simplified design can be comprised of a sample stage that provides only translation motion, but the additional rotation motion allows projections to be acquired at multiple projection angles about two rotation axes that can potentially lead to better 3D reconstruction results.

As illustrated in FIG. 3B, the beam 222 attaches to only one side of the sample mounting plate 90 and translation and rotation stage 56 to prevent mechanical conflict with the detector 52 during stage rotation.

In a typical design, the light objective lens 112 will have a NA in the range of 0.1 to 0.9. Larger NA objective lenses are preferred because they provide higher lateral resolution determined by $\delta_f = 0.61\lambda/NA$ and better depth resolution as $\delta_d = 1.22\lambda/(NA)^2$. In certain special applications, immersion lenses with NA from 0.5 up to 1.4 can also be used. A typical visible light detector 114 is the CCD or CMOS image sensor. CCD formats with larger number of pixels is preferred as it provides better sampling accuracy of the 2D image and better detection of rotation motion. Generally pixel format of at least 1,024×1,024 is preferred.

The alignment target, such as grid pattern 124, can be an intrinsic feature inside the sample or artificial features introduced in the sample or sample holder, as shown in FIG. 1. In the simplest design, a grid pattern 124 on the sample mounting plate 90 is used. However, this may cause confusion when the movement step is comparable to the grid spacing or when the rotation is about 90 degrees. Instead, a variable grid pattern with random spacing, or spacing based on prime number or chirp function is used to mitigate this problem.

In the cases when the sample is a semiconductor circuit board or packaging samples, the intrinsic features on the sample such as contact points can be used as the alignment markers. With wafer samples with interconnects fabricated on top of the wafer, the metrology system can be placed on top of the wafer to directly image these intrinsic features instead from below as shown.

While this invention has been particularly shown and described with references to preferred embodiments thereof, it will be understood by those skilled in the art that various changes in form and details may be made therein without departing from the scope of the invention encompassed by the appended claims.

What is claimed is:

1. A metrology system integrated into an X-ray laminography or tomography system, comprising:
    an illumination source for illuminating an alignment target;
    an objective lens;
    a spatially resolved detector for detecting images of the alignment target formed by the objective lens; and
    a stage system that rotates a sample of the laminography or tomography system and the alignment target.

2. A metrology system as in claim 1, wherein the illumination source produces infra-red light.

3. A metrology system as in claim 1, wherein the illumination source produces visible light.

4. A metrology system as in claim 1, wherein the illumination source produces ultra-violet light.

5. A metrology system as in claim 1, wherein the objective lens has a numerical aperture of 0.1 to 0.9.

6. A metrology system as in claim 1, wherein the objective lens is an immersion lens with an numerical aperture of 0.5 to 1.4.

7. A metrology system as in claim 1, wherein detector has at least 1,024×1,024 pixels.

8. A metrology system as in claim 1, further comprising a controller for shifting images from the laminography or tomography system in response to the images of the alignment target.

9. A metrology system as in claim 1, further comprising a controller for processing image from the laminography or tomography system to generate a 3D image in response to the images of the alignment target.

10. A metrology system as in claim 1, further comprising an objective lens stage for adjusting a focus position of the objective lens.

11. A metrology system as in claim 10, wherein the objective lens stage is a mechanical bearing stage.

12. A metrology system as in claim 10, wherein the objective lens stage is a flexure stage.

13. A metrology system as in claim 10, wherein the objective lens stage is driven by a DC motor.

14. A metrology system as in claim 10, wherein the objective lens stage is driven by a stepper motor.

15. A metrology system as in claim 10, wherein the objective lens stage is driven by a piezo-electric motor.

16. A metrology system as in claim 1, wherein the alignment target is a pattern fabricated a sample holder of the stage system.

17. A metrology system as in claim 16, where the pattern comprises a grid pattern.

18. A metrology system as in claim 17, where a grid pattern has variable spacing.

19. A metrology system as in claim 18, where the grid pattern has a random spacing.

20. A metrology system as in claim 18, where the grid pattern has a spacing based on prime number.

21. A metrology system as in claim 18, where the grid pattern has a spacing based on the chirp function.

22. A metrology method for a an X-ray laminography or tomography system, comprising:
    capturing X-ray images of a sample and rotating the sample between images;
    detecting optical images of the sample or a sample mounting system for each of the X-ray images;
    determining shifts in the sample between the X-ray images with reference to the optical images;
    shifting the X-ray images with respect to each other in response to the determined shifts in the optical images; and
    performing a reconstruction process on the shifted X-ray images to produce a three dimensional image of the sample.

23. A method as claimed in claim 22, wherein the step of detecting the optical images comprises detecting a pattern formed on a sample mounting plate.

24. A method as claimed in claim 22, further comprising determining vertical shifts in the sample by reference to focus changes in the optical images.

* * * * *